(12) United States Patent
Neal

(10) Patent No.: US 8,684,526 B2
(45) Date of Patent: Apr. 1, 2014

(54) COMPACT BINOCULAR ADAPTIVE OPTICS PHOROPTER

(75) Inventor: Daniel R. Neal, Tijeras, NM (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 629 days.

(21) Appl. No.: 12/829,691

(22) Filed: Jul. 2, 2010

(65) Prior Publication Data
US 2012/0002163 A1 Jan. 5, 2012

(51) Int. Cl.
- *A61B 3/08* (2006.01)
- *A61B 3/10* (2006.01)
- *A61B 3/02* (2006.01)
- *A61B 3/032* (2006.01)

(52) U.S. Cl.
CPC . *A61B 3/08* (2013.01); *A61B 3/032* (2013.01); *A61B 3/02* (2013.01)
USPC ............................ 351/201; 351/211; 351/239

(58) Field of Classification Search
USPC .......... 351/201, 205, 209, 211, 221, 239, 246
See application file for complete search history.

(56) References Cited

U.S. PATENT DOCUMENTS

| | | | |
|---|---|---|---|
| 6,155,684 A | 12/2000 | Bille et al. | |
| 7,195,354 B2 | 3/2007 | Olivier et al. | |
| 2004/0263786 A1 | 12/2004 | Williams et al. | |
| 2005/0030474 A1 | 2/2005 | Sumiya | |
| 2006/0017883 A1 | 1/2006 | Dai et al. | |
| 2007/0216867 A1 | 9/2007 | Campbell et al. | |
| 2007/0258046 A1 | 11/2007 | Lai | |
| 2008/0218694 A1* | 9/2008 | Chen et al. | 351/206 |
| 2008/0269731 A1 | 10/2008 | Swinger et al. | |
| 2008/0284979 A1 | 11/2008 | Yee et al. | |
| 2009/0244485 A1* | 10/2009 | Walsh et al. | 351/221 |

OTHER PUBLICATIONS

International Search Report and Written Opinion for Application No. PCT/US2011/042659, mailed on Nov. 4, 2011, 14 pages.
Freebody, "Optical simulator is all about vision," Institute of Physics and IOP Publishing, Oct. 19, 2009, 1 page total.

* cited by examiner

*Primary Examiner* — Mahidere Sahle
(74) *Attorney, Agent, or Firm* — AMO Wavefront Sciences, LLC

(57) ABSTRACT

A binocular vision apparatus allows a patient to view objects through the apparatus with polychromatic light and monochromatic aberration correction, such that the chromatic aberration of the eye can be combined with the monochromatic aberration correction, so as to provide a more accurate determination of vision quality. The binocular vision apparatus provides left and right viewing optics that can substantially maintain the line of sight of each eye, such that objects can be viewed in a room with 3D depth perception corresponding to the distance of the object from the patient. As both near and far objects can be viewed with binocular aberration correction, the patient can alternate binocular viewing between near and far vision with chromatic aberration so as to evaluate a proposed treatment such as a presbyopia correction.

45 Claims, 7 Drawing Sheets

| METHOD 200 | |
|---|---|
| 205 | Measure refraction and wavefront aberrations of right eye and left eye |
| 210 | Transmit measured wavefront refraction and wavefront aberrations of right eye and left eye to binocular viewing apparatus |
| 215 | Seat patient in chair in refracting lane for viewing an eye chart |
| 220 | Swing apparatus supported with arm into position in front of patient and align apparatus with pupils of patient |
| 225 | Adjust interpupillary distance of binocular viewing apparatus to correspond to interpupillary distance of patient |
| 230 | Adjust adjustable lens to correct defocus of wavefront measurement corresponding to spherical refractive error of right eye |
| 235 | Adjust deformable segmented mirror to correct astigmatism of wavefront measurement corresponding to cylindrical refractive error of right eye |
| 240 | Adjust deformable mirror to correct aberrations of right eye including one or more of coma, spherical aberration and trefoil |
| 245 | Measure vision of right eye with left eye occluded |
| 250 | Measures the position of the pupil with sensor. |
| 255 | Adjusts the aberration profile of the deformable mirror based on the position of the pupil. |
| 260 | Repeat steps 230-245 for left eye |
| 265 | Measure binocular far vision and binocular near vision |
| 270 | Deform mirror with aberrations corresponding to proposed treatment of each eye |
| 275 | Determine binocular far and near vision and patient satisfaction with proposed treatment for each eye |

FIG. 2

COMPACT BINOCULAR ADAPTIVE OPTICS PHOROPTER

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention is related to binocular vision and treatment of the eye.

People like to see. However, the eye can have defects that may result in less than ideal vision in at least some instances. For example, refractive errors of the eye can cause uncorrected vision to degrade. Refractive errors of the eye include nearsightedness, also referred to as myopia, farsightedness, also referred to as hyperopia, and astigmatism. These refractive errors can be treated with combinations of spherical lenses and cylindrical lenses, and the refractive prescription used to treat an eye, sometimes referred to as a refraction, can include a spherical optical power, a cylinder optical power and an axis of the cylinder. An example of a prior device that can be used to test vision with spherical and cylindrical lenses is the phoropter. The phoropter may contain different lenses used to measure refraction of the eye during sight testing and in at least some instances may be used to measure an individual's refractive error of both eyes to determine the eyeglass prescription.

Correction of the refractive error of the eye with spherical and cylindrical lenses may not fully correct at least some of the optical errors of the eye and can leave a patient with less than ideal correction in at least some instances. For example, the eye can have aberrations such as spherical aberration and coma that limit the effectiveness the refractive prescription that may be used with treatments such as spectacles and contact lenses. Also, although optical instruments such as microscopes, cameras, binoculars, telescopes and long range sighting (hereinafter "LRS") may correct for at least some optical errors of eye such as sphere, uncorrected spherical aberration and coma can limit vision with such optical instruments in at least some instances. As the eye ages, the ability of the eye to focus decreases such that people with good distance vision may wear corrective reading glasses to read. This age related decreased accommodation of the eye can be referred to as presbyopia.

The human eye can perceive color and the light used in many viewing situations includes more than one color of light. Natural light comprises polychromatic light having several colors. Although the human eye can perceive colors such as the primary colors red, blue and green, the human eye has chromatic aberration such that vision can be degraded when more than one color is viewed. Artificial light in many situations can include polychromatic light, for example florescent lights and incandescent lights. As chromatic aberration can affect measurements of the aberrations of the eye, many devices that measure aberrations of the eye rely on monochromatic light having only one wavelength of light or a narrow range of wavelengths.

Measurement of the monochromatic aberrations of the eye with wavefront sensors can allow for the correction at least some of the monochromatic optical errors of the eye. The monochromatic aberrations measured with wavefront sensors are sometimes referred to as wavefront elevation maps. While the wavefront elevation maps may show monochromatic optical errors of the eye as an elevation map of optical path distance from a reference plane, it can be helpful to decompose the wavefront map into orthogonal aberration terms, for example Zernike polynomials. With the polynomial approach, the second order terms correspond to sphere and cylinder of an eyeglass prescription. The sphere of an eyeglass prescription corresponds to the second order defocus term and the refractive cylinder of an eyeglass prescription corresponds to the second order astigmatism terms. The terms above second order of the polynomial decomposition can be referred to as high order aberrations.

Wavefront sensor measurements have been used to treat optical errors of the eye such as high order aberrations. For example, a laser can be programmed to ablate tissue of the eye based on the wavefront sensor measurement. However, at least some vision correction treatments such as refractive surgery, contact lenses, and intraocular lenses (hereinafter "IOLs") can induce high order aberrations of the eye. For example, the pupil may be larger than the proposed optical correction at night with some patients, such that at least some aberrations may result with night vision following treatment. It would be helpful to determine the effect of aberrations on vision and test the response of the patient to a treatment prior to the patient receiving treatment, such that the potential satisfaction of the patient with a proposed treatment can be determined. For example with laser eye surgery, it may be helpful to test the proposed treatment of the eye prior to ablation with the laser beam. Also, the treatment of presbyopia can include a multifocal lens that may induce aberrations that increase the depth of field of the eye, and it may be helpful to test the vision of the patient prior to treatment with the multifocal lens, for example.

At least some of the prior devices used to measure and test vision with aberrations prior to treatment such as surgery can perform less than ideally in at least some instances. For example, at least some of the prior devices that measure and correct monochromatic aberrations are not well suited for the evaluation of vision with polychromatic light. As normal vision can include polychromatic light, testing vision with monochromatic light may not provide a realistic assessment of vision with polychromatic light in at least some instances. Also, at least some of the prior devices determine vision with monocular viewing, and normal vision can be binocular such that testing a proposed treatment with monocular vision can be less than ideal.

Although some of the prior systems have tested binocular vision with aberration correction, these systems have produced less than ideal results in at least some instances. For example, at least some of the prior systems have relied on the patient viewing a target inside the apparatus in an artificial viewing environment that may not accurately assess vision. Also people can often be aware of their surroundings, and viewing an artificial target positioned inside the apparatus may result in the patient perceiving that he or she is looking inside the apparatus rather than at a remote target, such that the measurements can be less than ideal in at least some instances. Also, at least some of the prior binocular viewing systems may have flat target and in at least some instances may not present a three dimensional viewing environment for the patient to test vision as would occur normal vision in a room.

For the above reasons, it would be desirable to provide improved methods and apparatus for the determination of vision with aberration correction. Ideally such methods and apparatus would overcome at least some of the above mentioned deficiencies of the prior devices and provide an assessment binocular vision with aberration correction in a normal viewing environment that allows the patient to view his or her surroundings in polychromatic light with both near and far vision.

BRIEF SUMMARY OF THE INVENTION

Embodiments of the present invention provide improved methods and apparatus for the determination binocular vision with aberration correction, and can be used in many applications where binocular vision is helpful such as binocular vision testing, vision testing prior to eye surgery, and vision testing of pilots. Although specific reference is made to the determination of binocular vision of a patient in a clinic for treatment, embodiments can be used in many applications where binocular vision is used such as 3D displays, aerospace and machine vision.

The binocular vision apparatus can allow the patient to view objects through the apparatus with monochromatic aberration correction and polychromatic light, such that the chromatic aberration of the eye can be combined with the monochromatic aberration correction when vision is tested, so as to provide a more accurate determination of vision quality. Also, the binocular vision apparatus provides left and right viewing optics that can substantially maintain the line of sight of each eye, such that objects can be viewed in a room with 3D depth perception corresponding to the distance of the object from the patient. As both near and far objects can be viewed with binocular aberration correction, the patient can alternate binocular viewing between near and far vision with chromatic aberration so as to evaluate a proposed treatment such as a presbyopia correction. The binocular viewing apparatus can include optics to deflect the optical path transverse to the line of sight such that a distance between the patient's pupil and the entrance pupil to the apparatus can be decreased and the line of sight of objects near the patient corresponds substantially to the line of sight without correction. Also, the entrance pupil to the apparatus may correspond to the pupil of the patient so as to provide a more natural viewing experience. For example, an image of the patient's pupil formed can be formed near the entrance to the apparatus and the binocular viewing of the object through the apparatus may correspond to the patient's vision when the correction is placed on the eye, for example with surgery or a contact lens. The optical path extending transverse to the patient's line of sight can permit the apparatus to be easily positioned in front of the patient, for example positioned with an adjustable arm when the patient sits in a chair, such that the apparatus can be readily aligned to the patient by a health care provider. The binocular viewing apparatus may comprise an optical path deflecting prismatic component coupled to the deformable mirror and disposed along the optical path extending transverse to the line of sight such that the optical path crosses itself and the image of the viewing target seen by the patient is not inverted and properly oriented and such that the dimensions of the apparatus transverse to the line of sight can be decreased. The optical path deflecting prismatic component may comprise one or more of a geometric prism, a wedge, an inclined outer portion of a lens, a grating, a diffractive element or a micro-optic.

In a first aspect, embodiments provide a method of measuring vision of an eye of a person with an identifiable viewing target positioned away from the person. The eye has a pupil and a line of sight. The eye of the person is positioned at a location to view the target such that the eye has the line of sight extending from the pupil to the identifiable viewing target. Light of the viewing target is deflected away from the line of sight toward a deformable mirror. Light from the deformable mirror is reflected when the mirror is deformed with an aberration profile. The light reflected from the deformable mirror is deflected along the line of sight toward the eye such that the line of sight is maintained when the eye views the identifiable target with the aberration profile.

In many embodiments, the light is deflected away from the line of sight with a first mirror, and the light is deflected along the line of sight with a second mirror. The deformable mirror is positioned along an optical path between the first mirror and the second mirror such that the line of sight is maintained when the mirror deforms to adjust aberrations with the aberration profile.

In many embodiments, the optical path extends between the first mirror and the second mirror and a majority of the optical path extends transverse to the line of sight so as to decrease a separation distance between the first mirror and the second mirror, such that the line of sight is substantially maintained when the person views the target with light reflected from the first mirror.

In many embodiments, an image of the pupil is formed between the first mirror and the target to define an entrance pupil, and the line of sight extends through the entrance pupil. An image of a second pupil of a second eye on a second side of the person may be formed to define a second entrance pupil opposite the entrance pupil, The second eye may have a second line of sight, and the second line of sight may extend through the second entrance pupil to measure binocular vision of the person.

In many embodiments, an adjustable lens is positioned between the first mirror and the target at a location corresponding to the entrance pupil, and the adjustable lens is imaged near the pupil to compensate for spherical refractive error of the eye. The adjustable lens comprises one or more of a variable focal length lens or a liquid lens.

In many embodiments, a defocus of the eye is adjusted by moving one lens relative to another lens.

In many embodiments, the deformable mirror comprises at least about 30 discrete segments, each segment adjustable with a tip, a tilt and a length to correct a cylindrical refractive error of the eye and adjust the aberrations, and the segments of the deformable mirror are imaged near the pupil of the eye to correct the cylindrical refractive error and adjust the aberrations. The segments of the deformable mirror comprises a stroke length of at least about 30 um so as to correct at least about 5 D of cylinder across a 5 mm pupil.

In many embodiments, the line of sight corresponds to a substantially straight line extending from a virtual image of the pupil formed with the cornea of the eye, in which the line of sight extends from a center of the virtual image of the pupil along the substantially straight line to the identifiable target so as to define a binocular viewing angle between the eye, the target and a second line of sight of a second binocular eye when the person views the identifiable target without correction. The binocular viewing angle is maintained when light is deflected with the second mirror to the pupil.

In many embodiments, the deformable mirror is adjusted to compensate for cylinder of the person.

In many embodiments, the deformable mirror is adjusted to correct high order aberrations of the person. The high order aberrations may comprise one or more of spherical aberration, coma or trefoil.

In many embodiments, a position of the pupil is measured and an aberration profile of the deformable mirror is adjusted based on the position of the pupil.

In another aspect embodiments of the present invention provide method of measuring binocular vision of a pair of eyes of a person with an identifiable viewing target positioned away from the person, in which the pair of eyes comprise a left eye on a left side of the person and a right eye on a right side of the person. The right eye has a right pupil and a right line of sight, the left eye has a left pupil and a left line of sight. The pair of eyes is positioned at a location to view the target, such that the right eye has the right line of sight extending from the right pupil to the identifiable viewing target so as to define a right eye binocular viewing angle. The left eye has the left line of sight extending from the left pupil to the identifiable viewing target to define a left eye binocular viewing angle. An optical support is positioned having a right side and a left side such that the right side is aligned with right eye and the left side is aligned with the left eye. The right side supports a right side deformable mirror to adjust aberrations of the right eye, and the left side supports a left side deformable mirror to adjust aberrations of the left eye. Light is reflected from the right side deformable mirror to the right eye such that the right eye binocular viewing angle is maintained and light is reflected from the left side deformable mirror to the left eye such that the left eye binocular viewing angle is maintained.

In many embodiments, the person views the identifiable viewing target with depth perception when the right eye aberrations are adjusted with the right mirror and the left eye aberrations are adjusted with the left mirror.

In many embodiments, the person has an interpupillary distance between the right pupil and the left pupil and wherein the right side of the support is separated from the left side of the support with a separation distance, and the separation distance is adjusted in response to the interpupillary distance so as to maintain the left eye viewing angle and the right eye viewing angle. The right side deformable mirror moves with the right side support and the left side deformable mirror moves with the left side of the support.

In another aspect, embodiments provide an apparatus to measure an eye of a person with an identifiable viewing target positioned away from the apparatus, the eye having a pupil with a line of sight extending from the pupil to the viewing target. A support is sized for placement between the eye and the identifiable viewing target to align an optical path with the eye. A first mirror is positioned on the support to receive light from the identifiable viewing target and deflect the optical path away from the line of sight. A deformable mirror positioned on the support to reflect light from the first mirror with an aberration profile. A second mirror is positioned on the support to deflect light from the deformable mirror along the line of sight.

In many embodiments, a viewing angle of light incident on the first mirror is maintained with light reflected from the second mirror to the pupil when the person views the identifiable target with the aberration correction.

In many embodiments, the optical path between the first mirror and the second mirror extends a first cumulative distance along a first direction transverse to the optical axis of the eye. The optical path extends between the first mirror and the second mirror a second cumulative distance along a section direction corresponding the optical axis of the eye. The first cumulative distance is greater than the second cumulative distance so as to decrease a separation distance between the first mirror and the second mirror.

In many embodiments, the separation distance corresponds to a distance from a center of the first mirror to a center of the second mirror, and the separation distance comprises no more than about 3 inches (75 mm) to deflect the light from the second mirror substantially along the line of sight.

In many embodiments, the deformable mirror is positioned on the support with an orientation such that the second direction extends substantially along a reflective surface of the deformable mirror.

In many embodiments, the support comprises a plate extending transverse to the optical axis of the eye and wherein the first distance extends in at least one direction substantially along the plate. The plate can extend substantially along a plane and wherein the first distance extends in the at least one direction substantially along the plane.

In many embodiments, the second mirror and the deformable mirror are arranged to project an image of the pupil toward the first mirror to form an entrance pupil when the second mirror is aligned with the pupil such that the light from the identifiable viewing target approaches the entrance pupil at a viewing angle of the entrance pupil and wherein the light is reflected from the second mirror so as to approach the pupil at the viewing angle.

In many embodiments, an adjustable lens positioned between the first mirror and the identifiable viewing target at a location corresponding to the entrance pupil and wherein the adjustable lens is imaged near the pupil to compensate for spherical refractive error of the eye. A first lens can be disposed along the optical path between the first mirror and the deformable mirror, and a second lens can be disposed along the optical path between the second mirror and the deformable mirror. At least one lens can be positioned along the optical path between at the deformable mirror and the first lens and the second lens, wherein the optical path extends transverse to the line of sight from the first mirror to the second mirror.

In many embodiments, the at least one lens comprises one lens having a cross sectional size corresponding to a size of the first lens combined with a size of the second lens. The optical path extends from the first lens to a first portion of the one lens and the optical path extends from the second lens to a second portion of the one lens. The first portion of the one lens is located away from a center of the one lens opposite the first lens to deflect the optical path toward the deformable mirror with prism of the one lens. The second portion of the one lens is located away from the center opposite the second lens and opposite the first portion to deflect the optical path toward the mirror with prism of the one lens such that the optical path from the first lens to the first portion crosses the optical path from the second lens to the second portion. This crossing of the optical path can decrease substantially a dimension of the apparatus transverse to the line of sight and can also produce images of the viewing target as seen by the patient that are upright, non-inverted, and not flipped, such that the person can perceive the viewing target with correct orientation.

In many embodiments, the first lens has a first focal length and the second lens has a second focal length, wherein the first focal length corresponds to the second focal length such that the pupil is imaged near the adjustable lens with a magnification of about one and the line of sight is maintained when the pupil is positioned at a distance from the second lens corresponding to the second focal length. The first lens may comprise a first portion of a larger lens and the second lens comprises a second portion of the larger lens, wherein the optical path is deflected with prism of the first portion and prism of the second portion. The first lens may comprise one or more of a spherical lens, an apsheric lens, a micro optic, a diffractive optic, or a GRIN (gradient index) lens and the second lens comprises one or more of a spherical lens, an apsheric lens, micro optic, a diffractive optic, or a GRIN (gradient index) lens.

In many embodiments, the at least one lens has a focal length and the at least one lens is positioned a distance from the deformable mirror, the distance corresponding to the focal length of the at least one mirror such that the deformable mirror and at least one lens comprise a substantially telecentric configuration. The at least one lens may comprise one or more of spherical lens, an aspheric lens, a micro optic, a diffractive optic, or a GRIN (gradient index) lens.

In many embodiments, at least one prism positioned near the at least one lens to deflect light from the first lens at a first angle toward the deformable mirror and to deflect light from the deformable mirror at a second angle toward the second lens, in which the first angle corresponds to the second angle such that the viewing angle is maintained.

In many embodiments, a first prism is positioned near the first lens to deflect the optical path near the first lens and couple the optical path to the at least one prism and a second prism near the second lens to couple to the at least one prism and deflect the optical path near the second lens to maintain the viewing angle.

In many embodiments, the at least one prism comprises one or more of a wedge, a micro optic, a diffractive optic, or a GRIN (gradient index) prism.

In many embodiments, the adjustable lens comprises an adjustable lens, for example an electrostatic adjustable lens, having a range of spherical adjustment of at least about 10 D and wherein the deformable mirror comprises at least about 30 discrete segments, each segment adjustable with a tip, a tilt and a piston to correct a cylindrical refractive error of the eye and adjust the aberrations. The adjustable lens and the segments of the deformable mirror can be imaged near the pupil of the eye to correct the spherical and cylindrical refractive error of the eye and to adjust the aberrations.

In many embodiments, a sensor is configured to measure a position of the pupil, and the sensor and the deformable mirror are coupled to circuitry to adjust a profile of the deformable mirror based on the position of the pupil. Alternatively or in combination, the second mirror may comprise an adjustable mirror coupled to the sensor so as to adjust the second mirror based on the position of the pupil such that location of the image of the pupil on the deformable is substantially maintained when the pupil moves.

In another aspect embodiments provide an apparatus to measure binocular vision a right eye and a left eye of a person with a viewing target positioned away from the apparatus. The right eye has a right pupil, and the left eye has a left pupil, in which the pupil of the right eye is separated from the pupil of the left eye with an interpupillary distance. The apparatus comprises a right optical assembly and a left optical assembly. The right optical assembly is configured to couple the right eye. The right optical assembly comprises a first right lens oriented toward the target to view the target, a second right lens oriented toward the pupil to align with the pupil of the eye, and a right deformable mirror disposed along a right optical path between the first right lens and the second right lens. The left optical assembly is configured to couple to the left eye.

The left optical assembly comprises a first left lens oriented toward the target to view the target, a second left lens oriented toward the pupil to align with the optical axis of the eye, and a left deformable mirror disposed along left optical path between the first left lens and the second left lens. A linkage is coupled to the right optical assembly and the left optical assembly so as to adjust a separation distance of the right deformable mirror from the left deformable mirror in response to the interpupillary distance.

BRIEF DESCRIPTION OF THE DRAWINGS

FIG. 1C-1 shows an apparatus to correct aberrations and provide binocular vision with depth perception having a pupil alignment sensor, in accordance with embodiments of the present invention;

FIG. 2 shows a method 200 of determining binocular vision with aberration adjustment to each eye, in accordance with embodiments of the present invention.

DETAILED DESCRIPTION OF THE INVENTION

Figure 1A:
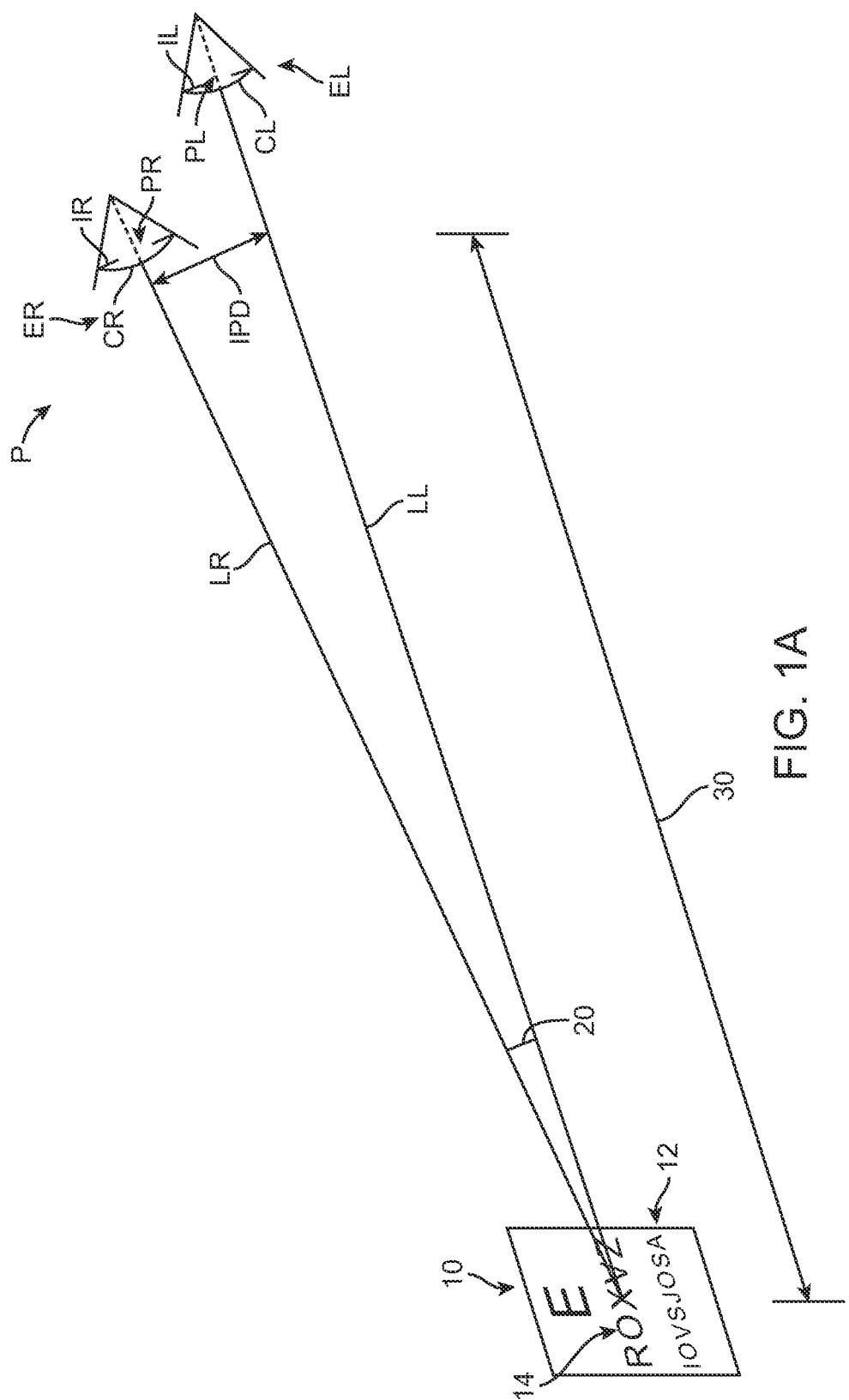
FIG. 1A shows binocular vision of a person viewing an eye chart with a plurality of identifiable characters suitable for incorporation of a binocular vision apparatus that corrects aberrations of each eye, in accordance with embodiments of the present invention.

Embodiments of the present invention are well suited for providing binocular vision with aberration adjustment, for example partial or full correction, such that the vision of the eyes can be tested in a normal viewing environment such as a room. The embodiments as described herein can be used to evaluate many forms of vision correction such as refractive surgery, contacts, spectacles, orthokeratology, IOLs and LRS designs, for example. Evaluation of binocular vision with adjustment to an amount of aberration can be helpful to determine diagnosis and treatment, and the embodiments as described herein allow the health care provider such as an optometrist, an ophthalmologist, a certified ophthalmic technician, or an optician to adjust the aberrations provided to the patient so as to test different amounts of aberration with binocular vision such that the patient and health care provider can evaluate aberration correction prior to treatment in a natural viewing environment. For example, with contacts, spectacles and IOLs correcting refractive error comprising sphere, cylinder and axis of the eye, there can be at least some aberration remaining when the ophthalmic lens is combined with the eye to correct vision, and it can be helpful to evaluate the quality of binocular patient vision with such ophthalmic lenses. With wavefront based correction of vision, the targeted treatment can include a customized treatment of all of the measured aberrations of the eye, or a portion of the measured aberrations, and the embodiments as described herein can be used to determine amounts of aberration correction that are sufficient to achieve a targeted visual acuity. For example with tissue ablation of the cornea to correct vision, the ablation profile of the cornea to correct aberrations may be somewhat irregular and it can be helpful to evaluate the contribution of these aberrations to both near and far binocular vision prior to treatment.

In at least some instances, it can be helpful to provide at least some aberration to the eye, and the embodiments as described herein provide binocular evaluation of amounts of aberration so as to determine the amounts of aberration for treatment. For example, treatment of presbyopia can include increasing at least some aberrations of the eye so as to increase the depth of field of the eye, and it can be helpful for the patient and health care provider to evaluate specific aberrations that may be added to increase the depth of field of the eye so as to determine appropriate amounts of each aberration for presbyopia treatment. Presbyopia treatment can include a binocular component with one eye corrected for near vision and the other eye corrected for distance vision, such that the amount of induced aberrations that increase the depth of field can be decreased. The amount of increased depth of field induced with aberrations of each eye can be combined with the amount of near vision correction or far vision correction of each eye, and the amounts of aberration and near or far vision correction of each eye can be varied so as to determine an effective binocular presbyopia treatment that is well tolerated by the patient. The binocular vision of the patient can be evaluated at both near and far vision with the adjusted aberrations in manner that corresponds to actual use by the patient, for example viewing a distance object such as an eye chart on a wall and viewing a near object such as a book held by the patient or a computer display.

Diagnosis and treatment of the progression of developmental myopia during formative growth years can benefit from improved measurement of aberrations. It has been shown that peripheral retinal defocus during formative growth years can be a potential a cause of myopia progression. Among several efforts to reduce this progression, specialized contact lenses that have a peripheral add power have been shown to be effective. Essentially these lenses add spherical aberration of a specific form and magnitude to the total wavefront through the eye of the patient. However, without a measurement of the initial content of the subject eye aberrations, it is difficult to determine the correct add power. It may be that the subject eye already has some spherical aberration content, and so the additional peripheral power may be too much or too little to have an effect. With the use of the adaptive optics phoropter instrument as described herein, the eye care practitioner can determine, for example through subjective feedback, whether the peripheral add power is adversely or beneficially affecting the subject's vision. The eye care practitioner can also determine the amount of the peripheral add power that is sufficient to reduce myopia progression.

As used herein a prism encompasses an optical component that deflects light, and may comprise one or more of a geometic prism, a wedge, an inclined outer portion of a lens, a grating, a diffractive element or a micro-optic.

The object viewed with the apparatus may comprise one or more of a physical object, printed text, a printed eye chart, a resolution target, a projection screen, a computer display, or an image of an object shown on a screen, an image of an object shown on a computer display, or the printed pages of a book.

Embodiments as described herein can also be used to test aberrations that may be induced by refractive surgery so as to ensure that the patient can tolerate aberrations such as spherical aberration and coma that may be induced by the refractive surgery.

As used herein an aberration correction encompasses amounts aberration used to treat vision of the eye such as amounts of aberration to decrease aberration and increase visual acuity and amounts of aberration adjusted, for example increased, so as to treat presbyopia, for example.

As used herein, like numerals and letters denote similar methods, elements, structures, and functions.

FIG. 1A shows binocular vision of a person, for example a patient P, viewing an eye chart with a plurality of identifiable characters suitable for incorporation of an binocular vision apparatus that corrects aberrations of each eye. The patient P has a first eye, for example a right eye ER, and a second eye, for example a left eye EL. The right eye ER and the left eye EL as separated by an interpupillary distance IPD that comprises the distance between the pupils of the eyes. The right eye ER has a right cornea CR to refract light and a right iris IR that defines a right pupil PR. The left eye EL has a left cornea CL to refract light and a left iris IL that defines a left pupil PL. An eye chart 10 can be positioned in front of patient P at a distance 30. For example, the eye chart 10 may comprise an eye chart for measuring distance vision that can be positioned on a wall of an office at a distance from the patient such as a Snellen eye chart at eight feet from the patient, a LogMAR eye chart, a contrast sensitivity eye chart with angled gratings or a low contrast visual acuity eye chart. Alternatively or in combination, the eye chart may comprise an eye chart for measuring near vision such as a Jaeger eye chart positioned twelve inches from the eyes of the patient, or one or more of the above eye charts having the characters scaled down in size for the measurement of near vision. The eye chart 10 comprises a plurality of identifiable viewing characters 12, such as letters, numbers, symbols, gratings at angles or hieroglyphs. In reading the eye chart 10, the patient P may fixate on an individual identifiable character 14 and attempt to identify the character. The patient can fixate sequentially on a plurality of identifiable characters so as to scan across a line of the eye chart with binocular vision and fixation. When the patient P fixates on the identifiable character, the right eye ER and the left eye EL converge on the character so as to define a right eye line of sight LR and a left eye line of sight LL. The line of sight of each eye can extend from the pupil to the fixation target such as the individual identifiable character 14, so as to define a viewing angle for each eye and a binocular viewing angle 20 between the eyes. The viewing angle 20 can be determined based on the interpupillary distance IPD and the distance 30 between the patient and the eye chart. The viewing angle 20 between the eyes can be related to the perceived distance of the eye chart 10 and characters 12 such that the person views the eye chart with depth perception.

The line of sight of the patient can be determined with respect to the pupil of the patient defined by the iris as viewed from outside the patient when the patient fixates on a target. The pupil and iris viewed from outside the patient may comprise a virtual image of the pupil and iris. The virtual image of the pupil and iris are formed based on the optical power of the cornea and proximity of the real pupil and real iris to the cornea. Although the optical power of the cornea can be about 40D, the real iris and real pupil are located near the cornea such that the virtual image of the pupil and iris corresponds substantially to the real pupil and real iris and may be used interchangeably in at least some embodiments as described herein.

Figure 1B:
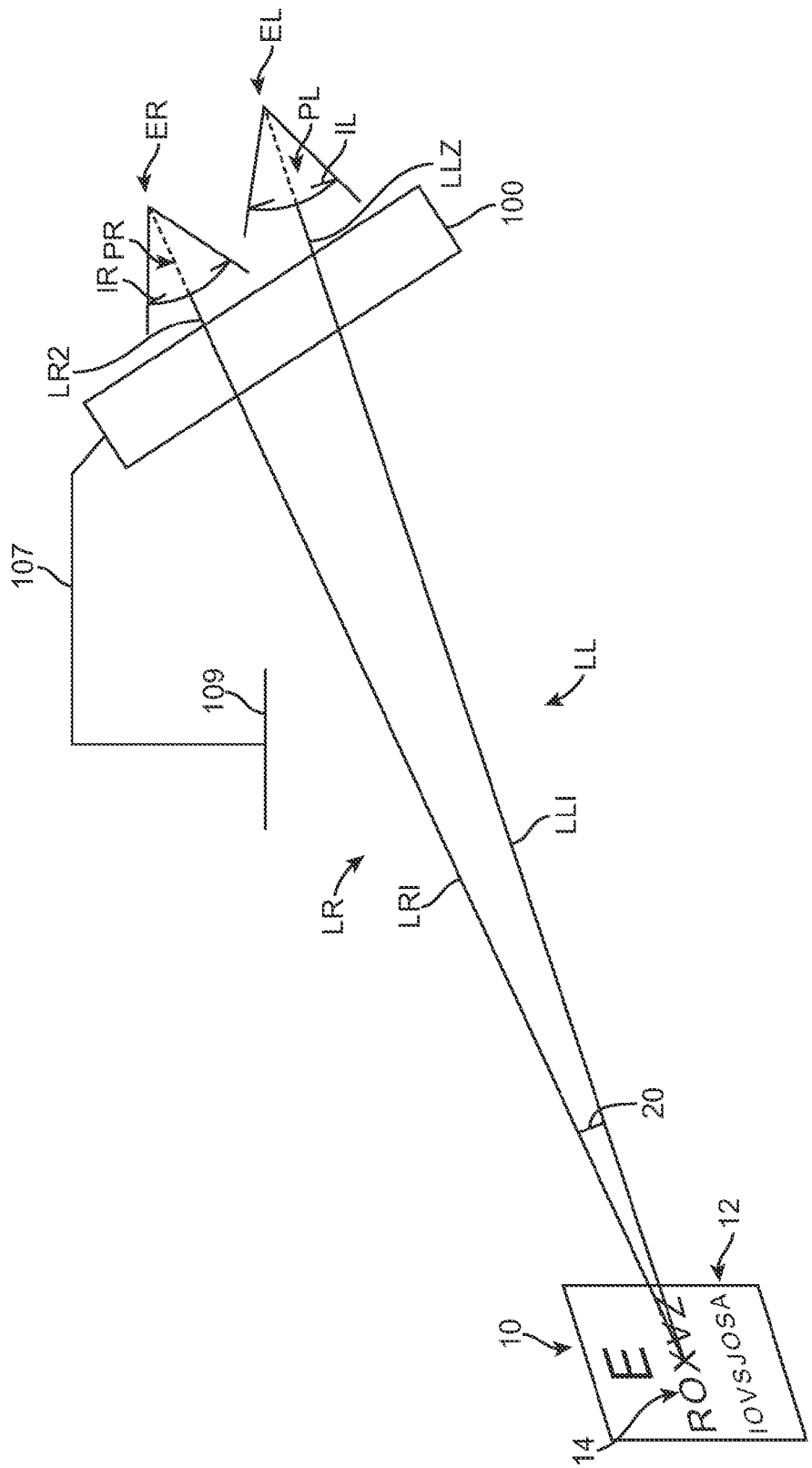
FIG. 1B shows the person viewing the eye chart with a binocular vision apparatus that corrects aberrations of each eye with depth perception, in accordance with embodiments of the present invention.

FIG. 1B shows the person viewing the eye chart with a binocular vision apparatus 100 that corrects aberrations of each eye with depth perception. The apparatus 100 is positioned between the patient P and the eye chart 10 such that the line of sight of each eye and binocular viewing angle 20 is substantially maintained. The apparatus 100 can be supported with an arm 107 attached to a base 109 such that the apparatus 100 can be swung in front of the patient P. The right eye line of sight LR may comprise a first component LR1 extending from individual identifiable character 14 to a right entrance pupil of apparatus 100 and a second component LR2 extending from apparatus 100 to the right pupil PR, and the first component LR1 is aligned substantially collinearly with the second component LR2 to within about 2 degrees, such that the right eye line of sight LR is substantially maintained. The alignment to maintain the line of sight so as to improve vision measurement as described herein can be determined empirically by a person of ordinary skill in the art based on the teaching described herein, and can be more than two degrees, or less than two degrees, for example to within about 1 degree or less, for example to within about 0.5 degrees. The left eye line of sight LL may comprise a first component LL1 extending from individual identifiable character 14 to a left entrance pupil of apparatus 100 and a second component LL2 extending from apparatus 100 to the left pupil PL, and the first component LL1 is aligned substantially collinearly with the second component LL2 to within about 2 degrees, for example as described above. Based on the teachings described herein, apparatus 100 can be constructed so as to maintain collinear alignment of the first component of the line of sight with the second component of the line of sight in accordance with tolerances of a standard refracting lane of an eye clinic. For example, an eye clinic may having a viewing target at a distance from the patient and the patient may have in interpupillary distance that can be combined to determine the viewing angle 20. The viewing target can be at about 20 feet or less depending on the refracting lane, for example about 4 meters from the patient corresponding to a vergence of about 0.25 Diopters. The patient may have an interpupillary distance of about 3 inches such that the viewing angle 20 is about 0.7 degrees at about 20 feet, and the half angle corresponding to each eye is about 0.35 degrees for the distance corresponding to the vergence of about 0.25 D. The viewing target can be closer, for example about 2 meters from the patient, corresponding to a vergence of about 0.5 D and a viewing angle 20 of about 2 degrees, and the first component of the line of sight can be maintained collinearly to within about one degree of the second component, for example. The collinear alignment of the first component and the second component can be similarly maintained for near vision correction. For example with at least some near vision eye charts the distance can be about one foot and the tolerances can be appropriately maintained, for example to within about 5 degrees or less at about one foot.

Figure 1C:
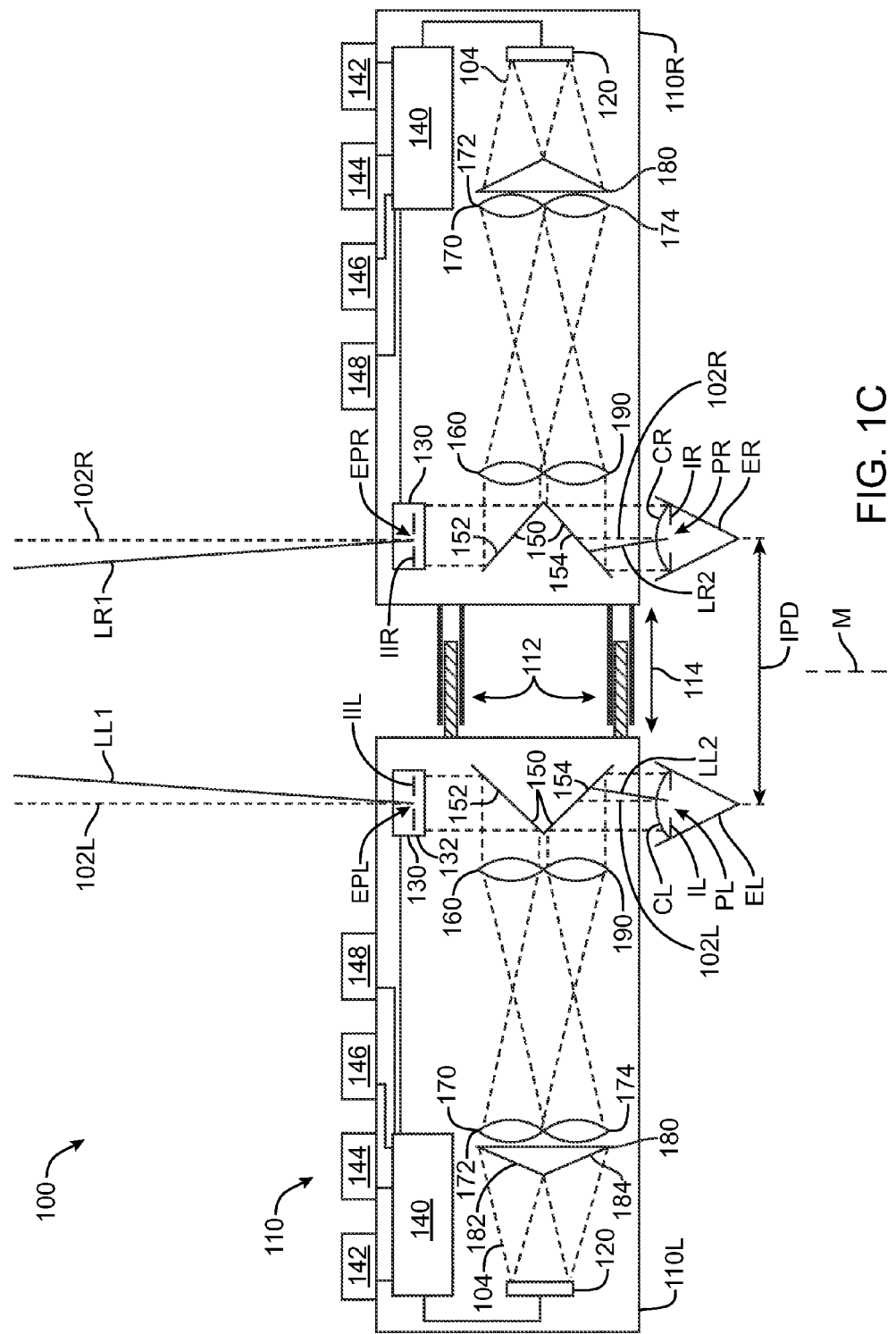
FIG. 1C shows an apparatus to correct aberrations and provide binocular vision with depth perception, in accordance with embodiments of the present invention.

FIG. 1C shows components apparatus 100 to provide binocular vision with aberration correction and depth perception. Apparatus 100 comprises a support 110 to support components of the apparatus, a deformable mirror 120 to provide aberrations, an adjustable component 130 to compensate for spherical defocus of the eye, circuitry 140 coupled to the deformable mirror 120 and adjustable component 130 to provide adjustable amounts aberration, and a pair of mirrors 150 to decrease a separation distance of the entrance pupil of the apparatus from a pupil of the eye to maintain the line of sight. The apparatus 100 comprises an internal optical path 104 that extends transverse to the line of sight such that a separation distance between the pair of mirrors 150 can be decreased. The pair of mirrors 150 disposed on each side comprises a first mirror 152 and a second mirror 154. The internal optical path 104 on the right side corresponds to an optical axis 102R on the right side and the internal optical path 104 on the left side corresponds to an optical axis 102L on the left side.

The components disposed along the optical path are arranged such that the patient sees the viewing target as he or she would with the proposed optical correction such as surgical optical correction. For example, the optical path for each eye is arranged such that the image of the eye chart 10 appears upright and non-inverted and is oriented similarly as would be seen by the patient without the viewing apparatus. The patient may also read a book with polychromatic light for example, and switch from far vision to near vision and vice versa to evaluate the optical correction such as a presbyopia correction. The components disposed along the optical path may provide at least some correction of chromatic aberration of the apparatus 100 such that the patient can view the eye chart 10 or other object with amounts of chromatic aberration corresponding to the proposed vision correction under test. For example, lenses of the apparatus 100 may comprise one or more of at least one achromatic lens or at least one diffractive optic so as to correct chromatic aberrations of the apparatus 100, such that the patient can view objects with polychromatic light and experience vision with monochromatic aberration correction and amounts chromatic aberration corresponding to vision of the eye with the proposed treatment under test. As the apparatus 100 can allow the eye to view the eye chart 10 or other object with polychromatic light and the eye's own chromatic aberration, the vision of the patient with the proposed correction under test can be similar to what the patient can expect following treatment such as laser eye surgery, IOL implantation, or other optical correction. Also, the eye can be tested with a red filter or a green filter positioned along optical path 104 such that a health care provider can determine the refraction of the eye with aberration correction.

The pair of mirrors 150 is coupled to the optical path 104 and the optical axes on each side of the support 110 such that the viewing angle is maintained. The first component of the right eye line of sight LR1 is coupled to the first mirror 152 and the second component of the right eye line of sight LR2 is coupled to the second mirror 154 such that the second component extends from the second mirror toward the pupil at the viewing angle and such that the line of sight LR is maintained. The viewing angle of the right eye may correspond substantially to the angle of the right side optical axis 102R to the right eye line of sight LR and each of the components thereof. The first component of the left eye line of sight LL1 is coupled to the first mirror 152 and the second component of the left eye line of sight LL2 is coupled to the second mirror 154 such that the second component extends from the second mirror toward the pupil at the viewing angle and such that the line of sight LL is maintained. The viewing angle of the left eye may correspond substantially to the angle of the left side optical axis 102L to the left eye line of sight LL and each of the components thereof. The angle of inclination of the first mirror 152 and the second mirror 154 can be determined such that the line of sight is maintained. The mirror may comprise one or more of many types of mirrors such as metallic mirrors, dichoric mirrors, pellicle beam splitters, and polarizing beam splitters.

The support 110 supports the components of the apparatus 100 and allows for placement and adjustment to the patient. The support 110 comprises a right side support 110R and a left side support 110L. The right side support 110R is coupled to the left side support 110L with an adjustable linkage 112. The linkage 112 may comprise one or more of sliding rails, telescopic tubes, rods pivots, or gears such that a separation distance 114 extending between the right support 110R and the left support 110L can be adjusted based on the interpupillary distance IPD so as to align optics of the right support with the right pupil PR and optics of the left support with the left pupil PL.

The deformable mirror 120 can be deformed under computer control so as to provide adjustable aberrations to the eye. The deformable mirror 120 can be positioned along the optical path 104 such that deformable mirror 120 is imaged along the optical path at a location near the pupil of the eye to provide adjustable aberration correction. For example, the deformable mirror 120 can be imaged on the pupil, on the cornea to test vision for corneal refractive surgery, or in front of the cornea at a location where spectacles are worn, for example. The deformable mirror may comprise one or more of many deformable mirrors suitable for the correction of vision such as a MEMS segmented deformable mirror or a thin membrane mirror. The segmented mirror may comprise a deformable mirror having from about 30 to about 100 mirror segments. The segmented MEMS mirror may comprise an array of mirror segments in which the distance of the each mirror segment along the optical path can be adjusted so as to correspond to an elevation of the wavefront at a location corresponding to the segment, for example. Deformable mirrors are commercially available from one or more known companies such as Flexible Optical (also referred to as "OKO Optical") of the Netherlands, Iris AO, Inc. of Berkeley, Calif., Xinetics (Northrop Grumman), or Boston Micromachines Corporation, for example. The segments may comprise a stroke length to position the mirror segment at a distance along the optical path and a tip angular adjustment and a tilt angular adjustment to incline the surface of the mirror in relation to the optical path. The stroke length may correspond to an elevation of the wavefront and the tip and tilt may correspond to the angle of inclination for the mirror segment. For example, a maximum stroke length of each mirror segment may comprise at least about 30 um to provide an optical path displacement of at least about 60 um that corresponds to about 5 D of cylinder for a 5 mm pupil, for example, and the tip and tilt adjusted at local angles that correspond to at least about 5 Diopters of cylinder at a 5 mm pupil, for example. This range of cylinder correction with the deformable mirror can correct for refractive error and measure cylinder for at least a majority of patients of a population. The segmented mirror may comprise a low hysteresis mirror, such that the deformable mirror can be operated in an open loop manner in that the deformable mirror is programmed with aberration corrections without subsequent aberration measurement to confirm that the mirror has deformed to the targeted shape profile.

The adjustable component 130 to compensate for spherical defocus of the eye may comprise one or more of an adjustable optic, an adjustable lens 132, a movable optic, a liquid adjustable lens, a movable lens, a movable mirror, or an optic mounted on a movable support. The adjustable component 130 can correct spherical refractive defocus error of the eye over a range of spherical refractive error, for example from about −10 D to about +5 D, for example from about −15 D to about +10 D. The adjustable lens may comprise a lens with moveable internal lens components, for example a liquid lens. The liquid lens may comprise a lens commercially available from Varioptic of Lyon, France, or other commercial sources, for example. The adjustable lens may comprise a spatial light modulator or other variable focus module, for example. The adjustable component 130 may comprise a movable mirror that changes an optical path length between lenses so as to correct the spherical defocus refractive error. The adjustable component may comprise a lens that moves relative to other components of the system, for example with the deformable mirror as described with reference to FIG. 1E described herein.

While the deformable mirror 120 can be combined with the adjustable component 130 in many ways, work in relation to embodiments suggests that the liquid lens combined with the segmented mirror having stroke length, tip and tilt can significantly decrease the size of the apparatus for placement in front of the patient supported with the arm. For example, the liquid lens can have an adjustable range of at least about 15 D, for example, and can be combined with the segmented deformable mirror having stroke length, tip and tilt so as to provide a compensation of spherical refractive error over a range of at least about 15 D and a correction of refractive cylinder of at least about 5 D.

The circuitry 140 can be coupled to the deformable mirror 120 and the adjustable component 130 so as to test binocular vision of the patient. The circuitry 140 may comprise a user interface for the health care provider to adjust the aberrations of the deformable mirror 120, for example. The circuitry 140 may comprise logic and drive circuitry to drive the components of the deformable mirror, and the circuitry 140 may comprise communication circuitry to communicate with other devices, for example to communicate with a wavefront measurement system. The communication circuitry may comprise serial communication circuitry, for example, and may comprise wireless communication circuitry, for example circuitry programmed with a Bluetooth® communication protocol to communicate among devices of the office of the health care provider. The circuitry 140 may comprise at least one processor comprising a tangible medium having programmable instructions of a computer readable medium embedded thereon so as to control the deformable mirror and the adjustment component 130 in response to user input.

The circuitry 140 may comprise a plurality user inputs so as to control aberrations and the vision correction during testing of the patient. The inputs may comprise an input for each eye and the inputs for each eye may comprise a sphere input 142, a cylinder input 144, a spherical aberration input 146 and a coma input 148. Additional inputs for additional aberrations such as trefoil and sixth order spherical aberrations can be provide. The inputs of the circuitry 140 may comprise inputs of a computer display coupled to circuitry 140. A commercially available wavefront system may measure the refractive error and all of the aberrations of the patient and transmit these measurements of each aberration to the circuitry 140, and this correction can be used as an initial evaluation of vision, and the aberrations adjusted by the eye care provider. Alternatively or in combination, a vision treatment such as a presbyopia correction or other correction can be input to circuitry 140.

The first lens 160 is positioned along optical path 104 and may comprise an optical power and focal length so as to form an image of the pupil near the adjustable component 130, for example near the adjustable lens 132. For example, first lens 160 can be positioned along the optical path at the focal length of first lens 160 from the adjustable lens 132 such that the image of the iris is formed within adjustable lens 132 when the iris of the eye is positioned at a focal length from the iris of the eye. The light received by lens 160 from lens 174 may comprise substantially collimated light such that the image of the iris is formed at the focal length of lens 160. The image of the iris formed with lens 160 may define the entrance pupil EPR. For example, iris IR and pupil PR can be imaged at the focal length of lens 160 to form an image of the iris IR and pupil PR that defines entrance pupil EPR inside adjustable optic 130 when iris IR and pupil PR are positioned at the focal length of lens 190. The first lens may comprise one or more of a spherical lens, an apsheric lens, micro optic, a diffractive optic, or a GRIN (gradient index) lens.

The second lens 190 is positioned along optical path 104 and may comprise an optical path and focal length so as to collimate substantially light from the pupil when the pupil is positioned at the focal length of the lens 190. The substantially collimated light from lens 190 is directed toward lens 172. The second mirror 154 can be inclined so as to reflect light to lens 172. The second lens may comprise one or more of a spherical lens, an apsheric lens, micro optic, a diffractive optic, or a GRIN (gradient index) lens.

Figures 1, 1C:
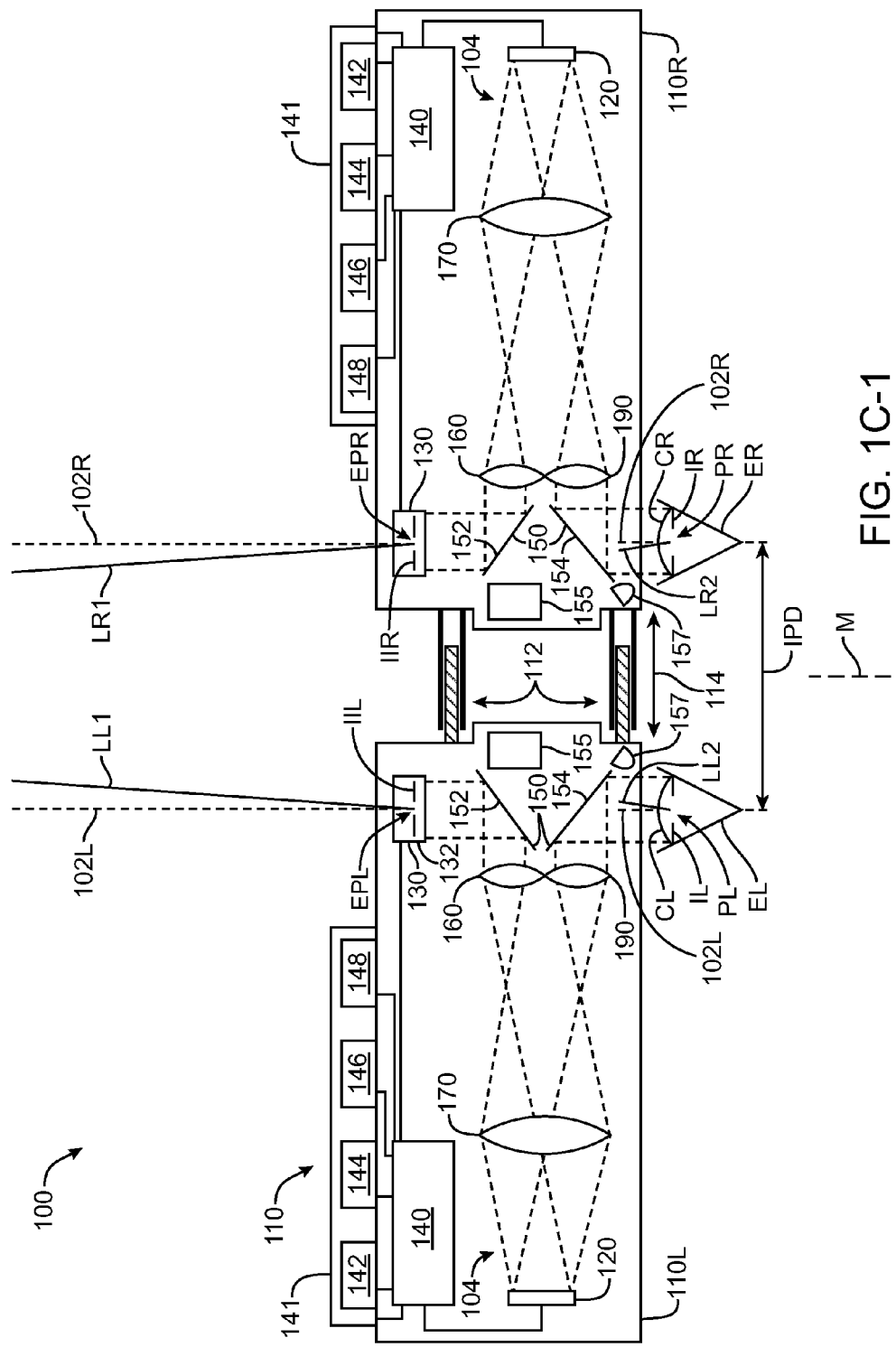
Figure 1D:
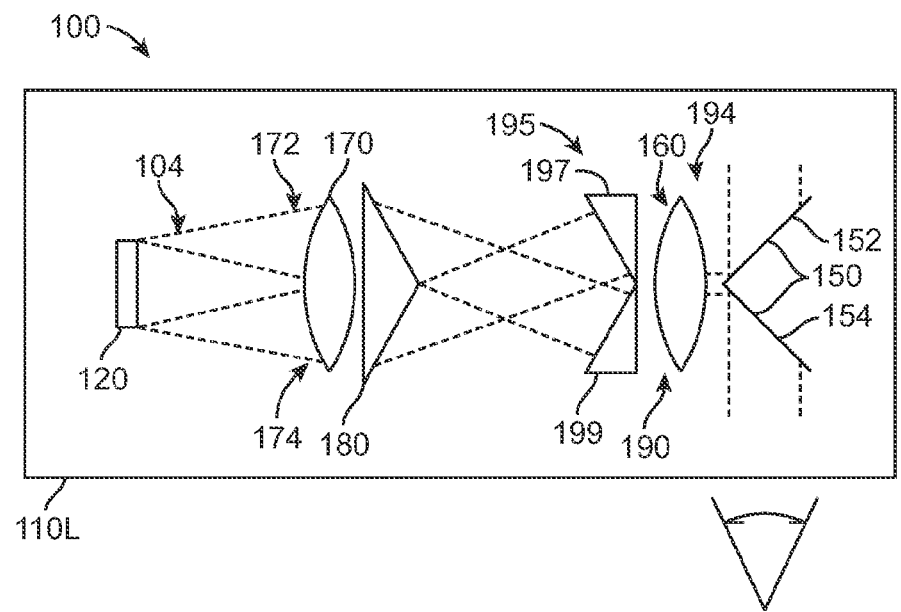
FIG. 1D shows an apparatus to correct aberrations and provide binocular vision with a first lens and a second lens in which the first lens comprises a first portion of a larger lens near a prism and the second lens comprises a second portion of the larger lens near the prism, in accordance with embodiments of the present invention.

A prism can be positioned near a larger lens sized such that a first portion of the larger lens comprises the first lens 160 and a second portion of the larger lens comprises the second lens 190, for example as shown with reference to FIG. 1D. Alternatively or in combination, the first mirror 152 and the second mirror 154 can have an angle such that the beam is appropriately deflected before the first lens 160 and after the second lens 190, respectively.

The at least one lens 170 comprises a first lens 172 and a second lens 174 positioned near at least one prism 180. The first lens 172 and the second lens 174 of the at least one lens 170 may comprise separate lenses. Alternatively, the at least one lens 170 may comprise a larger lens having a diameter at least as large as the combined diameters of lens 172 and lens 174, such that a first portion of the larger lens comprises lens 172 and a second portion of the larger lens comprises lens 174, for example as shown with reference to FIG. 1D. The at least one lens 170 has a focal length and the deformable mirror 120 is positioned along the optical path 104 at a distance from the at least one lens 170 corresponding to the focal length. The lens 172 has a focal length and the deformable mirror 120 is positioned at the focal length of lens 172 and the lens 174 has a focal length and the deformable mirror 120 is positioned at the focal length of lens 174, so as to comprise a substantially telecentric configuration. In some alternative embodiments, the lens and deformable mirror may comprise a non-telecentric configuration. The at least one lens may comprise one or more of a spherical lens, an apsheric lens, micro optic, a diffractive optic, or a GRIN (gradient index) lens. The lens 172 may comprise one or more of a spherical lens, an apsheric lens, micro optic, a diffractive optic, or a GRIN (gradient index) lens and the lens 174 may comprise one or more of a spherical lens, an apsheric lens, micro optic, a diffractive optic, or a GRIN (gradient index) lens.

The at least one prism 180 can be positioned near the at least one lens 170 so as to overlap substantially the optical path of lens 172 with lens 174 on the deformable mirror 120 and such that the optical path 104 crosses itself between the at least one lens 170 and lens 160 and lens 190. The at least one prism 180 can be helpful to provide images with the correct orientation when seen by the patient. The at least one prism 180 may comprise a first optical surface 182 corresponding to lens 172 and a second optical surface 184 corresponding to lens 174. The first optical surface 182 comprises optical power and can be inclined so as to deflect light from the deformable mirror through lens 172 and to lens 190. The second optical surface 184 comprises optical power and can be inclined so as to deflect light from the deformable mirror through lens 174 and to lens 160. The at least one prism 180 may comprise a diffractive component so as to correct chromatic aberration of the prism. The at least one prism may comprise one or more of a wedge, a micro optic, a diffractive optic, or a GRIN (gradient index) prism.

The optical components comprise a first imaging system located between the viewing target and deformable mirror 120, and a second imaging system located between the deformable mirror and the eye under test. The optics of the first imaging system can be arranged in such a way that light is collected from the target through adjustable element 130, off mirror 152, incident on lens 160, and hence onto lens 172 of at least one lens 170. Lens 160 and lens 172 can form a pair of imaging lenses such than an image from the approximate location of the adjustable component 130 is formed on the deformable mirror 120. After passing through lens 172, the light is redirected using prism 182 of at least one prism 180 to the deformable mirror 120. The prism 182 of at least one prism 180 may comprise one or more of a wedge, a grating, a diffractive element or a micro-optic.

After reflection and correction from deformable mirror 120, the reflected and corrected light is collected by components of the second imaging system that correspond to the components of the first imaging system. The components of the first imaging system incident on the deformable mirror 120 comprise lens 160, lens 172, and prism 182, as noted above. The corresponding components of the second optical system that collect light from the deformable mirror 120 comprise prism 184, lens 174 and lens 190. The light reflecting from the deformable mirror 120 is redirected with prism 184, and then collected and imaged with components of the second optical system comprising lens 174 and lens 190, such that an image of the deformable mirror is formed, through turning mirror 154, and onto the pupil of the eye under test. The components of the first optical system may correspond substantially to components of the second optical system, for example lens 160 may correspond to lens 190, lens 172 may correspond to lens 174, and prism 182 may correspond to prism 184, for example, such that the first optical system and the second optical system can be substantially parallel and equivalent. In many embodiments, the image that passes through the first optical system will be inverted and flipped left to right (hereinafter "LR"), and the image that passes through the second optical system will be inverted and flipped LR. Mirror 152 and mirror 154 will each result in one LR flip, so the net result is that the image will be upright and correct LR as viewed by the subject. Since the two optical systems are imaging systems, with object planes relayed to image planes, the net result is that the instrument will appear to the subject to have very little effective optical depth. This will help to maintain an easy subject interface as will not appear to the subject he/she is peering into an instrument, rather just looking through it at the viewing target.

FIG. 1C-1 shows the apparatus 100 to correct aberrations and provide binocular vision with depth perception having a pupil alignment sensor 155. The apparatus shown in FIG. 1C-1 may comprise many of the components as shown above. The sensor 155 can be positioned such that an image of the pupil is formed on sensor 152. The iris can be illuminated with illumination LED 157 so as to define the pupil of the eye with the illuminated iris, for example. The user interface 141 may comprise a touch screen display, for example. The inputs, as described above, may be shown on the touch screen display. The user interface 141 comprising the touch screen display may show an image of the pupil to the user. For example, user interface 141 comprising the touch screen display may comprise a first touch screen display on the left side supported with the left support component 110L, and a second touch screen display on the right side supported with the right support component 110R.

The at least one lens 170 may comprise a one lens having a distance across corresponding to about twice the distance across of lens 160 or lens 190, for example. The at least one lens 170 may comprise a focal length and can be positioned a distance from deformable mirror 120 that corresponds substantially to the at least one lens 170. The optical path 104 through the at least one lens 170 can extend through the one lens away from the center such that light is deflected with prismatic wedge the one lens away from the center. For example, the pair of lenses comprising lens 172 and lens 174 as shown above can be replaced with the at least one lens 170 comprising the one lens, and the optical path can be transmitted through the one at least one lens 170 at locations corresponding to lens 172 and lens 174, such that the optical path is substantially similar to the optical path as shown above with reference to FIG. 1C, for example. Alternatively or in combination, the at least one prism 180 as described above can be combined with the at least one lens 170 comprising the one lens. The mirror 152 and the mirror 154 can be adjusted such that the optical path extends through the one lens to the deformable mirror. A person of ordinary skill in the art can determine inclination of mirror 152 and mirror 154, such that the optical path 104 extends through the one lens to the deformable mirror 120. The one lens may comprise a single multi element lens such as an achromatic doublet, or triplet, for example.

The at least one lens 170 may comprise one lens having a cross sectional size corresponding to a size of the first lens 160 combined with a size of the second lens 190. The optical path extends from the first lens 160 to a first portion of the one lens 170 and the optical path extends from the second lens 190 to a second portion of the one lens 170. The first portion of the one lens 170 is located away from a center of the one lens 170 opposite the first lens 160 to deflect the optical path toward the deformable mirror 120 with prism of the one lens 170. The second portion of the one lens 170 is located away from the center opposite the second lens 190 and opposite the first portion so as to deflect the optical path toward the deformable mirror 120 with prism of the one lens 170 such that the optical path 104 from the first lens 160 to the first portion crosses the optical path 104 extending from the second lens 190 to the second portion of one lens 170. This crossing of the optical path can decrease substantially a dimension of the apparatus transverse to the line of sight and can also produce images of the viewing target as seen by the patient that are upright, non-inverted, and not flipped, such that the person can perceive the viewing target with correct orientation.

As the position of the pupil relative to the deformable mirror can alter the measured aberrations, it can be helpful to measure the position of the pupil and maintain alignment of the pupil during the operation of the apparatus 100. This measurement and alignment of pupil can be done by illuminating the subject eye with LED 157 and collecting and imaging light transmitted through mirror 152 with an image sensor 155, for example a CCD array. The LED 157 and image sensor 155 may comprise components of circuitry 140, as described above. The image sensor 155 can be positioned such that an image of the pupil of the eye is formed thereon with the optics of apparatus 100. Mirror 152 can be designed so as to transmit some at least light corresponding to wavelengths of LED 157. For example, mirror 152 may comprise a dichroic beamsplitter configured to transmit infrared or near infrared light, for example. Transmission wavelengths of mirror 152 can be matched to wavelengths of the illumination LED 157, for example. This system can allow determination of the pupil position and size with the image sensor 155. It may be helpful to couple a display to the image sensor 155 so as to provide feedback to the operator that the subject eye is in proper position. For example, the interface 141 of circuitry 140 may comprise touch screen LCD display coupled to the image sensor 155 to show the image of the pupil from the image sensor 155.

The apparatus 100 can be configured to adjust one or more of the deformable mirror 120 or lower mirror 154 in response to location of the pupil. The commands and control circuitry and software instructions of circuitry 140 can be coupled to the deformable mirror and can adjust the profile of the deformable mirror so as to correspond substantially, for example so as to match, the measured pupil position. Alternatively or in combination, the second mirror 154 may comprise an adjustable mirror, for example a movable mirror under control of the processor, such that an angle of the second mirror 154 can be adjusted based on measured position of the pupil so as to maintain the location of the image of the pupil on deformable mirror 120 when the pupil of the eye moves.

The apparatus 100 can be aligned to the patient based on the image of the left pupil shown on the display on the left side and the image of the right pupil shown on the right side of the apparatus 100. For example, the apparatus 100 can be raised or lowered in relation to the patient, and can be translated left to right in relation to the patient such that the apparatus can be aligned to the patient.

The interpupillary distance can be adjusted based on the pupil shown on the display of each side of apparatus 100. For example, an image of the pupil on each side of the patient can be shown on the touch screen display on each side of the patient, such that the user can adjust the interpupillary distance based on the image of the pupil shown on each side of apparatus 100.

FIG. 1D shows apparatus 100 to correct aberrations and provide binocular vision with first lens 160 and second lens 190 in which the first lens 160 comprises a first portion of a larger lens 194 near at least one prism 195 and the second lens 190 comprises a second portion of the larger lens 194 near the at least one prism 195. The at least one prism 195 may comprise a first prism 197 coupled to first lens 160 and second prism 199 coupled to second lens 190. The first prism 197 may comprise a first inclined surface to deflect the optical path and the second prism 199 may comprise a second inclined surface to deflect the optical path. The first and second inclined surfaces can be coupled to a diffractive optical surface to correct chromatic aberration, for example with a diffractive optical surface disposed on each of the respective inclined surfaces. The at least one prism 195 may comprise one or more of a wedge, a micro-optic, a diffractive optic, or a GRIN (gradient index) prism. In at least some embodiments, the at least one prism 195 wedge may not be used, as the lens at least one lens 170 can be used off-axis, for example. The at least one lens 170 may comprise one larger lens positioned near at least one prism 180.

Figure 1E:
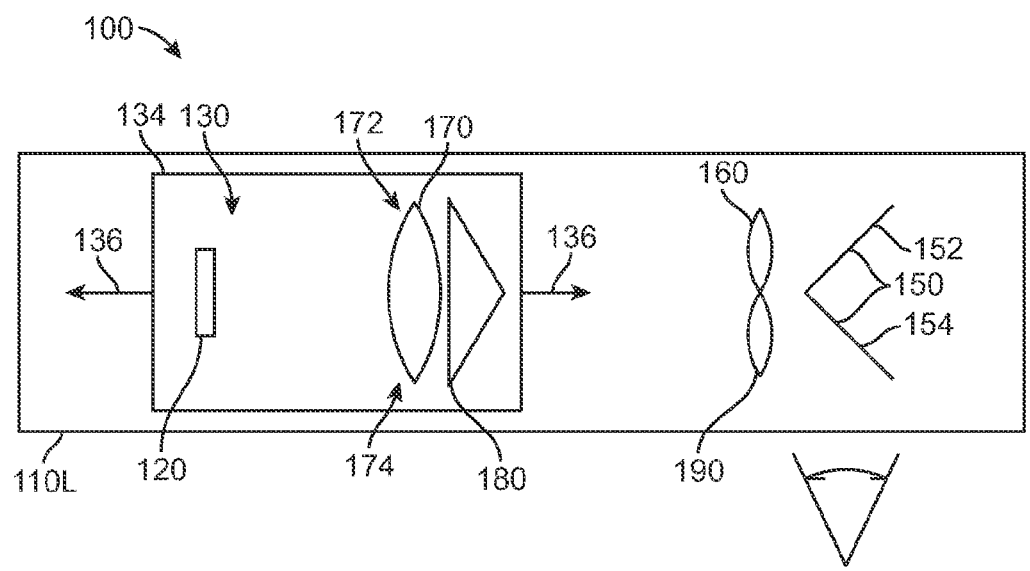
FIG. 1E shows adjustment of the apparatus to compensate for spherical defocus of the eye with a moving lens and prism, in accordance with embodiments of the present invention.

FIG. 1E shows adjustment of the apparatus 100 in which adjustable component 130 to compensate for spherical defocus of the eye comprises moving lenses. The adjustable component 130 may comprise a translatable support platform 133. The at least one lens 170, the at least one prism 180 and deformable mirror 120 can be positioned on the support platform 133 that translates so as to increase or decrease the optical path length as shown with arrows 136. This system can be arranged with at least one of either of the following configurations: individual lenses with wedge for example a shown in FIG. 1C as described above, or one large lens, for example as described above with reference to FIG. 1C-1. In these embodiments, the position of the optical elements on platform 130 relative to the lens 190 and the lens 160 determine a relationship between position as indicated with arrows 136 and optical power (Diopters). This relationship between position and optical power (Diopters) may be calibrated in advance so that the platform position can be used to determine the defocus compensation based on linear or non-linear look up or fit, for example. The adjustable component 130 may comprise an optometer, for example.

Figure 1F:
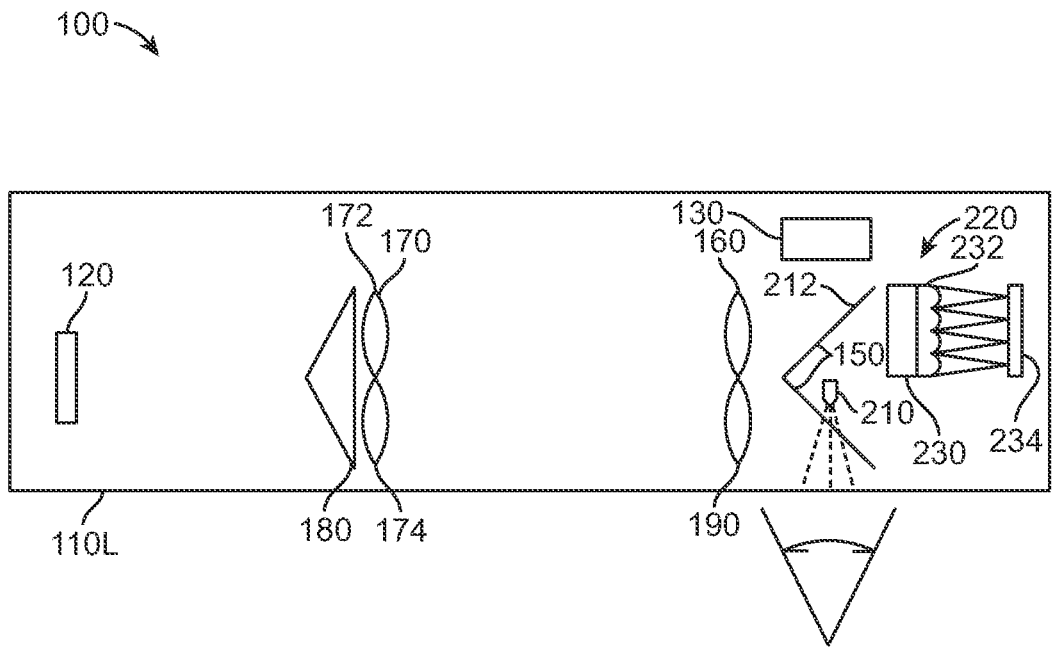
FIG. 1F shows the apparatus to provide binocular vision with aberration correction and adjustment having a Hartmann-Shack wavefront sensor, in accordance with embodiments of the present invention.

FIG. 1F shows the apparatus 100 to provide binocular vision with aberration correction and adjustment having a wavefront sensor 220, for example a Hartmann Shack wavefront sensor. The wavefront sensor 220 can receive light from mirror 152 that reflects visible light and transmits IR light. The wavefront sensor 220 may comprise a light source 210 such as a super luminescent diode to direct light energy such as IR light energy into the eye for reflection and measurement. A lenslet array 232 can be positioned to receive light and form spots on a detector array such as a CCD array.

The wavefront sensor 220 may be combined in many ways with the vision testing apparatus as described herein. For example, the wavefront sensor may measure the light that does not pass through the extra adjustable component 130. In such embodiments, the wavefront sensor may comprise a very large dynamic range lenslet array 232, or the wavefront sensor 220 may comprise an adjustable lens 230 similar to adjustable lens 130 as described above, or both. Alternatively, the wavefront sensor 220 may measure light through adjustable component 130, for example through the optometer of FIG. 1E, such that the defocus of the eye can be compensated by the lens position of the adjustable component 130, for example.

Figure 1G:
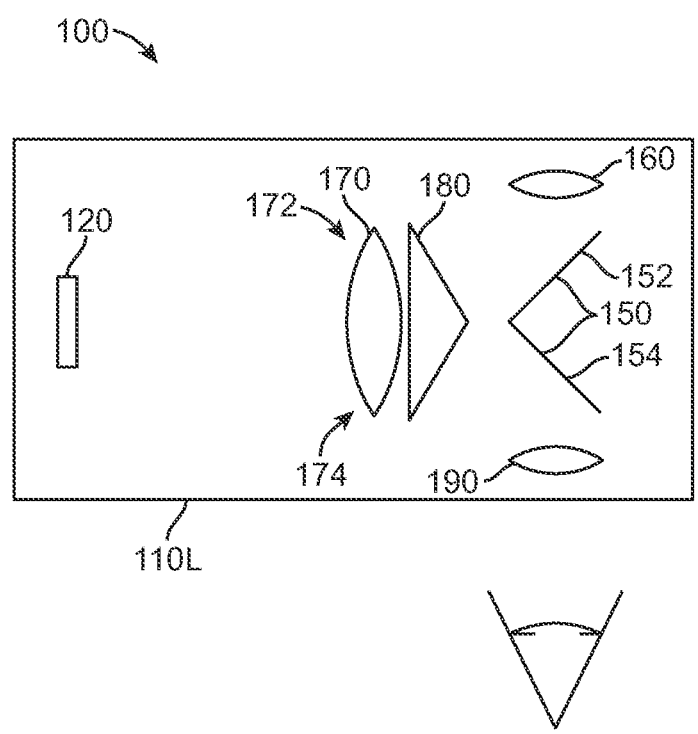
FIG. 1G shows the apparatus to provide binocular vision with aberration correction and adjustment having a lens and a prism to deflect the optical path toward and away from the deformable mirror such that the first lens comprises a first portion of a larger lens near the prism and the second lens comprises a second portion of the larger lens near the prism, in accordance with embodiments of the present invention.

FIG. 1G shows the left portion of the apparatus having the first lens 160 positioned along the optical path between the eye chart and the first mirror 152 and the second lens 190 disposed along the optical path between the second mirror 154 and the eye. This configuration can decrease the distance the light travels transverse to the line of sight from first mirror 160 to deformable mirror 120 and from deformable mirror 120 to second mirror 154. The second lens 190 can form an image of the iris and pupil on the deformable mirror 120 and the first lens 160 can re-image the first image of the iris and pupil on the deformable mirror so as to form a second image between first lens 160 and the viewing target. The second image of the pupil and iris comprises an aerial image of the pupil and the entrance pupil that is located between first lens 160 and the eye chart, such that the entrance pupil as described above is located in front of first lens 160. The at least one lens 170 is positioned near at least one prism 180, and the at least one lens has a focal length and the deformable mirror is positioned at approximately the focal length from the deformable mirror so as to comprise a substantially telecentric configuration, as described above. The at least one lens 170 has a first portion comprising lens 172 and a second portion comprising lens 174. The at least one prism 180 can deflect the optical path as described above.

FIG. 2 shows a method 200 of determining binocular vision with aberration adjustment to each eye.

A step 205 measures refraction and wavefront aberrations of right eye and left eye. A step 210 transmits measured wavefront refraction and wavefront aberrations of right eye and left eye to binocular viewing apparatus. A step 215 seats the patient in a chair in a refracting lane for viewing an eye chart. A step 220 swings the apparatus supported with the arm into position in front of patient and aligns apparatus with pupils of patient. A step 225 adjusts interpupillary distance of the binocular viewing apparatus to correspond to interpupillary distance of the patient. A step 230 adjusts the adjustable lens to correct defocus of wavefront measurement corresponding to spherical refractive error of right eye. A step 235 adjusts the segmented deformable mirror to correct astigmatism of wavefront measurement corresponding to cylindrical refractive error of right eye. The refractive error of the eye can be measured with many devices, for example an autorefractor, and can be entered manually, for example. A step 240 adjusts the deformable mirror to correct aberrations of right eye including high order aberrations such as one or more of coma, spherical aberration and trefoil. A step 245 measures vision of the right eye with the left eye occluded. A step 250 measures the position of the pupil with sensor. A step 255 adjusts the aberration profile of the deformable mirror based on the position of the pupil. Alternatively or in combination, the tilt or mirror 154 can be adjusted such that the pupil image location on the deformable mirror remains substantially fixed. Circuitry 140 as described above may comprise an eye tracker coupled to mirror 152 and adjust the mirror based on measured pupil position, for example. A step 265 measures binocular far vision and binocular near vision. A step 270 deforms the mirror with aberrations corresponding to the proposed treatment of each eye. A step 275 determines binocular far and near vision and patient satisfaction with proposed treatment for each eye.

It should be appreciated that the specific steps illustrated in FIG. 2 provide a particular method of determining binocular vision with aberration adjustment to each eye, according to an embodiment of the present invention. Other sequences of steps may also be performed according to alternative embodiments. For example, alternative embodiments of the present invention may perform the steps outlined above in a different order. Moreover, the individual steps illustrated in FIG. 2 may include multiple sub-steps that may be performed in various sequences as appropriate to the individual step. Furthermore, additional steps may be added or removed depending on the particular applications. One of ordinary skill in the art would recognize many variations, modifications, and alternatives.

As the above described methods and apparatus can be used to measure binocular vision, it will be appreciated that in some instances components of the apparatus and method are described with reference to one eye, for example the right eye, and that similar components and methods can be constructed and performed with the second eye, for example the left eye. For example, as the patient comprises a midline M and the apparatus comprises a right support component 110R and a left support component 110L, components described with respect to one side of the midline M, for example on left support 110L, it will be understood that similar components can be symmetrically disposed on the opposite side of the midline, for example on the second support 110R.

The above described figures and supporting text show methods and apparatus in accordance with some embodiments of the present invention. Many additional changes and alternate embodiments can be used, and some of these embodiments may have fewer or more optical components, and the locations of components and number of components employed can be changed so as to achieve binocular vision having the line of sight of each eye substantially maintained with upright properly oriented images. A person of ordinary skill in the art will recognized such changes and modifications based on the teachings described herein, and can construct experimental optics apparatus so as to determine empirically locations, orientations and components suitable to maintain the line of sight with properly oriented upright images without undue experimentation.

While the above is a complete description of the preferred embodiments of the invention, various alternatives, modifications, and equivalents may be used. Therefore, the above description should not be taken as limiting in scope of the present invention, which is defined solely by the appended claims and the full scope of the equivalents thereof.

What is claimed is:

1. A method of measuring vision of an eye of a person with a remote identifiable viewing target positioned away from the person at a viewing distance, the eye having a pupil and a line of sight, the method comprising:
    positioning the eye of the person at a location to view the remote target such that the eye has the line of sight extending from the pupil to the remote identifiable viewing target;
    deflecting light of the remote viewing target away from the line of sight toward a deformable mirror;
    reflecting light from the deformable mirror when the mirror is deformed with an aberration profile;
    deflecting the light reflected from the deformable mirror along the line of sight toward the eye such that the line of sight is maintained when the eye views the remote identifiable target with the aberration profile; and
    wherein the person views the remote identifiable viewing target in a natural viewing environment with three dimensional depth perception corresponding to the viewing distance of the remote identifiable viewing target from the person.

2. The method of claim 1 wherein the light is deflected away from the line of sight with a first mirror and wherein the light is deflected along the line of sight with a second mirror and wherein the deformable mirror is positioned along an optical path between the first mirror and the second mirror such that the line of sight is maintained when the mirror deforms to adjust aberrations with the aberration profile.

3. The method of claim 2, wherein the optical path extends between the first mirror and the second mirror and wherein a majority of the optical path extends transverse to the line of sight to decrease a separation distance between the first mirror and the second mirror such that the line of sight is substantially maintained when the person views the target with near vision.

4. The method of claim 2, wherein an image of the pupil is formed between the first mirror and the target to define an entrance pupil and wherein the line of sight extends through the entrance pupil.

5. The method of claim 4, wherein an image of a second pupil of a second eye on a second side of the person is formed to define a second entrance pupil opposite the entrance pupil and wherein the second eye has a second line of sight and wherein the second line of sight extends through the second entrance pupil to measure binocular vision of the person.

6. The method of claim 4, wherein an adjustable lens is positioned between the first mirror and the target at a location corresponding to the entrance pupil and wherein the adjustable lens is imaged near the pupil to compensate for spherical refractive error of the eye.

7. The method of claim 6, wherein the adjustable lens comprises one or more of a variable focal length lens or a liquid lens.

8. The method of claim 4, wherein a defocus of the eye is adjusted by moving one lens relative to another lens.

9. The method of claim 6, wherein the deformable mirror comprises at least about 30 discrete segments, each segment adjustable with a tip, a tilt and a length to correct a cylindrical refractive error of the eye and adjust the aberrations and wherein the segments of the deformable mirror are imaged near the pupil of the eye to correct the cylindrical refractive error and adjust the aberrations.

10. The method of claim 9, wherein the segments of the deformable mirror comprises a stroke length of at least about 30 um so as to correct at least about 5 D of cylinder across a 5 mm pupil.

11. The method of claim 1, wherein the line of sight corresponds to a substantially straight line extending from a virtual image of the pupil formed with the cornea of the eye, the line of sight extending from a center of the virtual image of the pupil along the substantially straight line to the identifiable target so as to define a binocular viewing angle between the eye, the target and a second line of sight of a second binocular eye when the person views the identifiable target without correction and wherein the binocular viewing angle is maintained when light is deflected with the second mirror to the pupil.

12. The method of claim 1, wherein the deformable mirror is adjusted to compensate for cylinder of the person.

13. The method of claim 1, wherein the deformable mirror is adjusted to correct high order aberrations of the person.

14. The method of claim 13, wherein the high order aberrations comprise one or more of spherical aberration, coma or trefoil.

15. The method of claim 1, wherein a position of the pupil is measured and an aberration profile of the deformable mirror is adjusted based on the position of the pupil.

16. A method of measuring binocular vision of a pair of eyes of a person with a remote identifiable viewing target in a natural viewing environment positioned away from the person at a viewing distance, the pair of eyes comprising a left eye on a left side of the person and a right eye on a right side of the person, the right eye having a right pupil and a right line of sight, the left eye having a left pupil and a left line of sight the method comprising:
    positioning the pair of eyes at a location to view the remote target such that the right eye has the right line of sight extending from the right pupil to the remote identifiable viewing target to define a right eye binocular viewing angle and such that the left eye has the left line of sight extending from the left pupil to the remote identifiable viewing target to define a left eye binocular viewing angle;
    positioning an optical support having a right side and a left side such that the right side is aligned with right eye and the left side is aligned with the left eye, wherein the right side supports a right side deformable mirror to adjust aberrations of the right eye and wherein the left side supports a left side deformable mirror to adjust aberrations of the left eye;
    wherein light is reflected from the right side deformable mirror to the right eye such that the right eye binocular viewing angle is maintained and light is reflected from the left side deformable mirror to the left eye such that the left eye binocular viewing angle is maintained; and
    wherein the remote identifiable viewing target, the left line of sight between the optical support and the viewing target, and the right line of sight between the optical support and the viewing target are external to the optical support.

17. The method of claim 16 wherein the person views the remote identifiable viewing target with depth perception corresponding to the viewing distance of the remote identifiable viewing target from the person when the right eye aberrations are adjusted with the right mirror and the left eye aberrations are adjusted with the left mirror.

18. The method of claim 16 wherein the person has an interpupillary distance between the right pupil and the left pupil and wherein the right side of the support is separated from the left side of the support with a separation distance and wherein the separation distance is adjusted in response to the interpupillary distance to maintain the left eye viewing angle and the right eye viewing angle and wherein the right side deformable mirror moves with the right side support and the left side deformable mirror moves with the left side of the support.

19. An apparatus to measure an eye of a person with a remote identifiable viewing target positioned external to the apparatus in a natural viewing environment, the eye having a pupil with a line of sight extending from the pupil to the viewing target, the apparatus comprising:
a support sized for placement between the eye and the remote identifiable viewing target to align an optical path with the eye;
a first mirror positioned on the support to receive light from the remote identifiable viewing target and deflect the optical path away from the line of sight;
a deformable mirror positioned on the support to reflect light from the first mirror with an aberration profile; and
a second mirror positioned on the support to deflect light from the deformable mirror along the line of sight; and
wherein the apparatus is configured such that the person views the remote identifiable viewing target s positioned external to the apparatus so that the line of sight between the deformable mirror and the viewing target extends away from and external to the apparatus with three dimensional depth perception corresponding to the viewing distance of the remote identifiable viewing target from the person.

20. The apparatus of claim 19 wherein a viewing angle of light incident on the first mirror is maintained with light reflected from the second mirror to the pupil when the person views the identifiable target with the aberration correction.

21. The apparatus of claim 19 wherein the optical path between the first mirror and the second mirror extends a first cumulative distance along a first direction transverse to the optical axis of the eye and wherein the optical path extends between the first mirror and the second mirror a second cumulative distance along a second direction corresponding the optical axis of the eye, the first cumulative distance greater than the second cumulative distance to decrease a separation distance between the first mirror and the second mirror.

22. The apparatus of claim 21 wherein the separation distance corresponds to a distance from a center of the first mirror to a center of the second mirror and wherein the separation distance comprises no more than about 3 inches (75 mm) to deflect the light from the second mirror substantially along the line of sight.

23. The apparatus of claim 21 wherein the deformable mirror is positioned on the support with an orientation such that the second direction extends substantially along a reflective surface of the deformable mirror.

24. The apparatus of claim 21 wherein the support comprises a plate extending transverse to the optical axis of the eye and wherein the first distance extends in at least one direction substantially along the plate.

25. The apparatus of claim 24 wherein the plate extends substantially along a plane and wherein the first distance extends in the at least one direction substantially along the plane.

26. The apparatus of claim 19 wherein the second mirror and the deformable mirror are arranged to project an image of the pupil toward the first mirror to form an entrance pupil when the second mirror is aligned with the pupil such that the light from the identifiable viewing target approaches the entrance pupil at a viewing angle of the entrance pupil and wherein the light is reflected from the second mirror so as to approach the pupil at the viewing angle.

27. The apparatus of claim 26 further comprising an adjustable lens positioned between the first mirror and the identifiable viewing target at a location corresponding to the entrance pupil and wherein the adjustable lens is imaged near the pupil to compensate for spherical refractive error of the eye.

28. The apparatus of claim 27 further comprising a first lens disposed along the optical path between the first mirror and the deformable mirror, a second lens disposed along the optical path between the second mirror and the deformable mirror and at least one lens positioned along the optical path between the deformable mirror and the first lens and the second lens, wherein the optical path extends transverse to the line of sight from the first mirror to the second mirror.

29. The apparatus of claim 28 wherein the at least one lens comprises one lens having a cross sectional size corresponding to a size of the first lens combined with a size of the second lens and wherein the optical path extends from the first lens to a first portion of the one lens and the optical path extends from the second lens to a second portion of the one lens and wherein the first portion of the one lens is located away from a center of the one lens opposite the first lens to deflect the optical path toward the deformable mirror with prism of the one lens and wherein the second portion of the one lens is located away from the center opposite the second lens and opposite the first portion to deflect the optical path toward the mirror with prism of the one lens such that the optical path from the first lens to the first portion crosses the optical path from the second lens to the second portion.

30. The apparatus of claim 28 wherein the first lens has a first focal length and the second lens has a second focal length, wherein the first focal length corresponds to the second focal length such that the pupil is imaged near the adjustable lens with a magnification of about one and the line of sight is maintained when the pupil is positioned at a distance from the second lens corresponding to the second focal length.

31. The apparatus of claim 28 wherein the first lens comprises a first portion of a larger lens and the second lens comprises a second portion of the larger lens, wherein the optical path is deflected with prism of the first portion and prism of the second portion.

32. The apparatus of claim 28 wherein the first lens comprises one or more of a spherical lens, an aspheric lens, a micro optic, a diffractive optic, or a GRIN (gradient index) lens and the second lens comprises one or more of a spherical lens, an aspheric lens, micro optic, a diffractive optic, or a GRIN (gradient index) lens.

33. The apparatus of claim 28 wherein the at least one lens has a focal length and wherein the at least one lens is positioned a distance from the deformable mirror, the distance corresponding to the focal length of the at least one mirror such that the deformable mirror and at least one lens comprise a substantially telecentric configuration.

34. The apparatus of claim 33 wherein the at least one lens comprises one or more of spherical lens, an aspheric lens, a micro optic, a diffractive optic, or a GRIN (gradient index) lens.

35. The apparatus of claim 33 further comprising at least one prism positioned near the at least one lens to deflect light from the first lens at a first angle toward the deformable mirror and to deflect light from the deformable mirror at a second angle toward the second lens, the first angle corresponding to the second angle such that the viewing angle is maintained.

36. The apparatus of claim 35 further comprising a first prism positioned near the first lens to deflect the optical path near the first lens and couple the optical path to the at least one prism and a second prism near the second lens to couple to the at least one prism and deflect the optical path near the second lens to maintain the viewing angle.

37. The apparatus of claim 35 wherein the at least one prism comprises one or more of a wedge, a micro optic, a diffractive optic, or a GRIN (gradient index) prism.

38. The apparatus of claim 27, wherein the adjustable lens comprises an adjustable lens having a range of spherical adjustment of at least about 10 D and wherein the deformable mirror comprises at least about 30 discrete segments, each segment adjustable with a tip, a tilt and a piston to correct a cylindrical refractive error of the eye and adjust the aberrations and wherein the adjustable lens and the segments of the deformable mirror are imaged near the pupil of the eye to correct the spherical and cylindrical refractive error of the eye and to adjust the aberrations.

39. The apparatus of claim 19 further comprising a sensor to measure a position of the pupil, the sensor and the deformable mirror coupled to circuitry to adjust a profile of the deformable mirror based on the position of the pupil.

40. The apparatus of claim 19 further comprising a sensor to measure a position of the pupil, the sensor coupled to circuitry and the second mirror to adjust the second mirror based on the position of the pupil.

41. An apparatus to measure binocular vision a right eye and a left eye of a person with a remote viewing target in a natural viewing environment positioned away from the apparatus at a viewing distance, the right eye having a right pupil, the left eye having a left pupil, the pupil of the right eye separated from the pupil of the left eye with an interpupillary distance, the apparatus comprising:
  a right optical assembly to couple the right eye, the right optical assembly comprising,
  a first right lens oriented toward the remote target to view the remote target;
  a second right lens oriented toward the pupil to align with the pupil of the eye; and
  a right deformable mirror disposed along a right optical path between the first right lens and the second right lens; and
  a left optical assembly to couple to the left eye, the left optical assembly comprising
  a first left lens oriented toward the remote target to view the remote target;
  a second left lens oriented toward the pupil to align with the optical axis of the eye; and
  a left deformable mirror disposed along left optical path between the first left lens and the second left lens; and
  a linkage coupled to the right optical assembly and the left optical assembly to adjust a separation distance of the right deformable mirror from the left deformable mirror in response to the interpupillary distance; and
  the apparatus configured such that the person views the remote identifiable viewing target positioned external to the apparatus with three dimensional depth perception corresponding to the viewing distance of the remote identifiable viewing target from the person.

42. The method of claim 1, wherein the remote identifiable viewing target further comprises a real target positioned in the natural viewing environment external to a viewing system, the viewing system including the deformable mirror.

43. The method of claim 1 further comprising viewing the remote identifiable viewing target from both eyes through the natural environment without a viewing system including the deformable mirror and establishing a right line of sight and a left line of sight with a viewing angle between the right line of sight and the left line of sight, and wherein the right line of sight and the left line of sight and the viewing angle is substantially maintained when the person views the viewing target with the viewing system relative to viewing the target without the viewing system.

44. The method of claim 43, wherein the right and left lines of sight extend from the viewing system to the remote viewing target external to the viewing system and through the natural viewing environment.

45. The apparatus of claim 29, wherein the deformable mirror is coupled to the prism of at least one lens positioned along the optical path to deflect the light toward the deformable mirror away from the line of sight and away from the deformable mirror towards the line of sight.

* * * * *